United States Patent [19]

Bailey

[11] Patent Number: 5,271,385

[45] Date of Patent: Dec. 21, 1993

[54] ABDOMINAL CAVITY ORGAN RETRACTOR

[75] Inventor: Robert W. Bailey, Reisterstown, Md.

[73] Assignee: United States Surgical Corporation, Norwalk, Conn.

[21] Appl. No.: 844,970

[22] Filed: Feb. 28, 1992

Related U.S. Application Data

[63] Continuation of Ser. No. 703,678, May 21, 1991, abandoned, which is a continuation-in-part of Ser. No. 501,241, Mar. 29, 1990, abandoned.

[51] Int. Cl.$^5$ ............................................. A61B 17/02
[52] U.S. Cl. ...................................................... 128/20
[58] Field of Search ............................................. 128/20

[56] References Cited

U.S. PATENT DOCUMENTS

| | | | |
|---|---|---|---|
| 972,983 | 10/1910 | Arthur | 606/198 |
| 987,173 | 3/1911 | Sale . | |
| 1,244,751 | 10/1917 | McCleary . | |
| 1,275,520 | 8/1918 | Bell | 128/20 |
| 1,328,624 | 1/1920 | Graham . | |
| 2,137,710 | 11/1938 | Anderson | 128/321 |
| 2,202,748 | 5/1940 | Solo | 128/20 X |
| 2,316,297 | 4/1943 | Southerland et al. | 128/326 |
| 2,518,994 | 8/1950 | Miller | 128/321 |
| 2,541,246 | 2/1951 | Held | 128/305 |
| 2,816,552 | 12/1957 | Hoffman . | |
| 3,313,294 | 4/1967 | Uddenberg | 128/20 |
| 3,314,431 | 4/1967 | Smith, Jr. | 128/200.26 |
| 3,467,090 | 9/1969 | Zollett | 128/131 |

(List continued on next page.)

FOREIGN PATENT DOCUMENTS

| | | |
|---|---|---|
| 0246086 | 11/1987 | European Pat. Off. . |
| 8303342 | 7/1983 | Fed. Rep. of Germany . |
| 2082987 | 11/1971 | France . |
| 468805 | 2/1952 | Italy . |
| 52-52388 | 4/1977 | Japan . |
| 53-94481 | 8/1978 | Japan . |
| 54-63992 | 5/1979 | Japan . |
| 57-193811 | 12/1982 | Japan . |
| 736949 | 5/1980 | U.S.S.R. . |
| 990220 | 6/1981 | U.S.S.R. . |
| 1251888 | 8/1986 | U.S.S.R. . |
| 1360708 | 12/1987 | U.S.S.R. . |

OTHER PUBLICATIONS

Product Bulletin PEL-OP 26 from Karl Storz Endoskope, no publication date.
Jamner Surgical Instruments, Inc. advertisement dated Oct. 1991.
Cabot Medical Corporation advertisement dated Jan. 1992.
Snowden-Pencer advertisement dated Apr. 1992.
Cooper Endoscopy advertisement dated Oct. 1992.
Optik Incorporated advertisement, p. 33, Jun. 1992 edition, Surgical Products.
Stephen L. Corson, M.D., "Two New Laparoscopic Instruments: Bipolar Sterilizing Forceps and Uterine Manipulator," Medical Instrumentation, vol. 11, No. 1, Jan.-Feb. 1977.

Primary Examiner—William H. Grieb

[57] ABSTRACT

A device which can be used in a laparoscopic surgical procedure is disclosed. The device is to be used in the surgical procedure as a retractor i.e. to displace and hold internal organs of a patient away from the organ which is the surgical objective. The device, which is essentially a long thin narrow tube, is partially inserted into the abdomen of a patient through a tiny incision in the abdomen wall. Retractor action is accomplished by the movement of levers, slides or buttons located on the end of the tube that remains outside of the patient. These levers, slides or buttons control the opening or closing of components, such as finger-like protuberances, that depend from the end of the tube that is within the patient. These protuberances push and hold floppy organs away from the surgical objective so that the surgical team can clearly view the organ using the laparoscope and remove the organ with tiny laparoscopic instruments. In this manner radical incisions, recovery time, and scarring are greatly reduced.

68 Claims, 11 Drawing Sheets

U.S. PATENT DOCUMENTS

| | | | |
|---|---|---|---|
| 3,517,128 | 6/1970 | Hines | 128/345 |
| 3,837,345 | 9/1974 | Matar . | |
| 3,858,586 | 1/1975 | Lessen | 128/6 X |
| 3,877,433 | 4/1975 | Librach | 606/119 |
| 3,934,589 | 1/1976 | Zimmer | 128/321 X |
| 3,938,527 | 2/1976 | Rioux et al. | 128/321 X |
| 3,964,468 | 6/1976 | Schulz | 128/321 X |
| 4,000,743 | 1/1977 | Weaver | 606/119 |
| 4,022,208 | 5/1977 | Valtchev | 604/55 |
| 4,130,113 | 12/1978 | Graham | 128/20 |
| 4,174,715 | 11/1979 | Hasson | 128/321 |
| 4,190,042 | 2/1980 | Sinnreich | 128/20 |
| 4,222,380 | 9/1980 | Terayama | 128/216 |
| 4,249,533 | 2/1981 | Komiya | 128/321 X |
| 4,393,872 | 7/1983 | Reznik et al. | 604/151 |
| 4,447,227 | 5/1984 | Kotsanis . | |
| 4,459,978 | 7/1984 | Kotsanis | 128/20 |
| 4,467,802 | 8/1984 | Maslanka | 128/321 |
| 4,557,255 | 12/1985 | Goodman | 128/7 |
| 4,598,699 | 7/1986 | Garren et al. | 128/4 |
| 4,654,028 | 3/1987 | Suma | 604/106 |
| 4,655,219 | 4/1987 | Petruzzi | 128/321 |
| 4,692,139 | 9/1987 | Stiles | 604/22 |
| 4,744,363 | 5/1988 | Hasson | 128/321 |
| 4,753,237 | 6/1988 | Puchy | 128/20 X |
| 4,765,311 | 8/1988 | Kulik et al. | 128/20 X |
| 4,909,789 | 3/1990 | Taguchi et al. | 604/107 |
| 4,936,823 | 6/1990 | Colvin | 604/106 |
| 4,994,079 | 2/1991 | Genese et al. | 606/206 |
| 5,010,892 | 4/1991 | Colvin | 128/774 |
| 5,081,983 | 1/1992 | Villalta et al. | 128/20 |

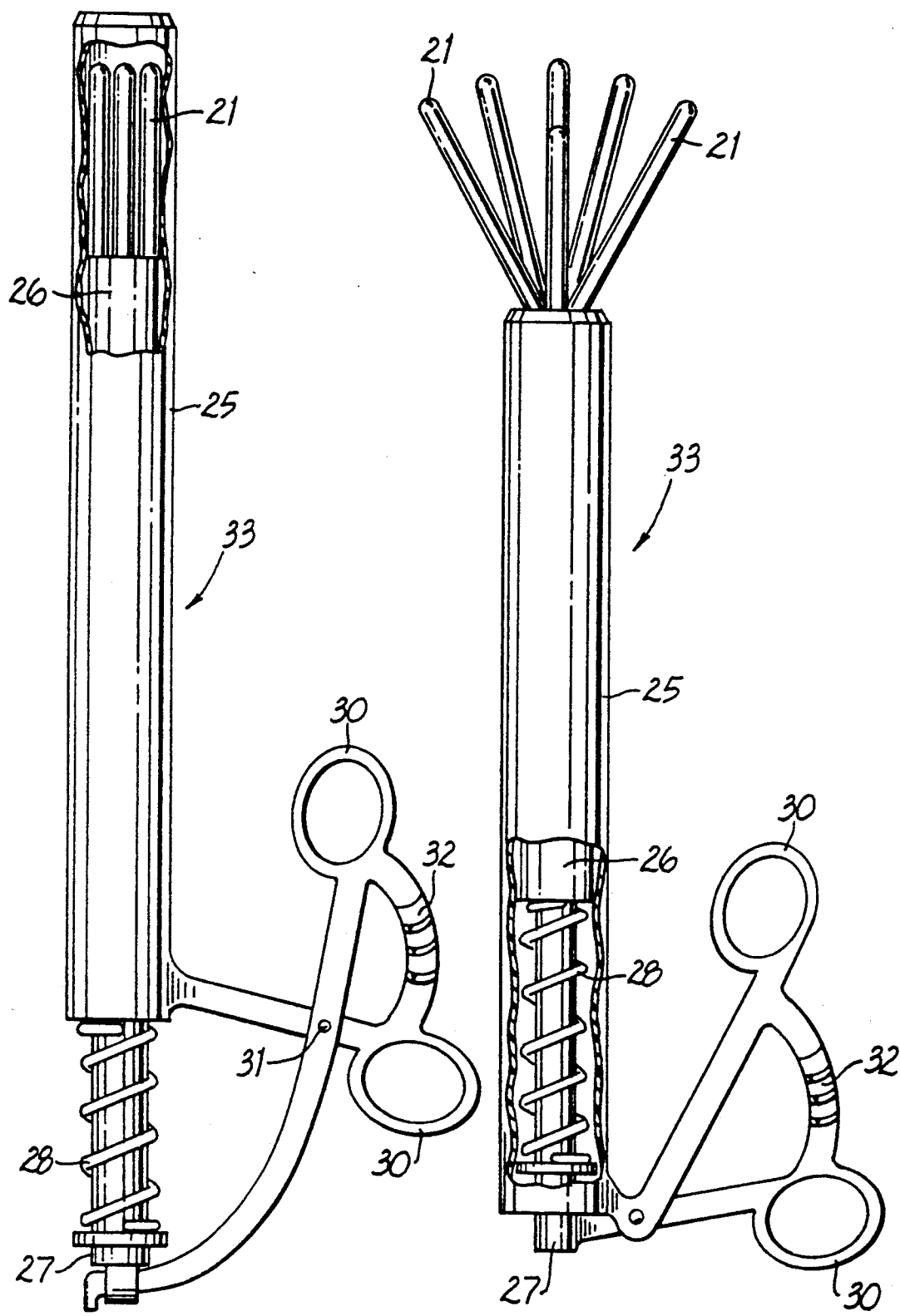

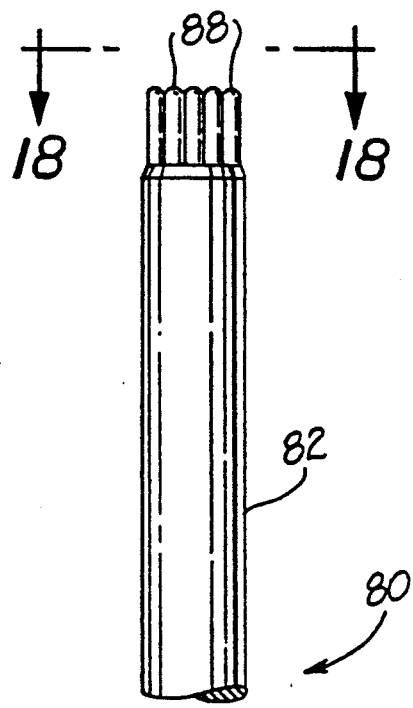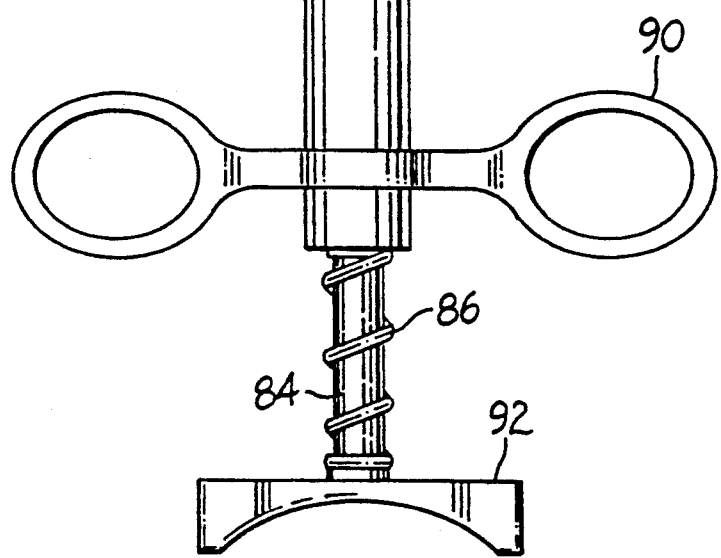
FIG.16

ABDOMINAL CAVITY ORGAN RETRACTOR

This is a continuation of copending application Ser. No. 07/703,678 filed on May 21, 1991, which is a continuation-in-part of Ser. No. 07/501,241 filed on Mar. 29, 1990, both now abandoned.

BACKGROUND OF THE INVENTION

1. Field of the Invention

This invention relates to the field of surgery, and in particular to devices which are known in the art as retractors.

2. Prior Art

A surgeon, when performing an operation on a patient, is often obstructed in his efforts to excise diseased or damaged tissues or organs by surrounding tissues, fatty deposits, arteries, or other organs. It has generally been the case, when performing gastro intestinal surgery, i.e. surgery within the abdominal cavity, to make a large cut in the abdomen wall to produce a suitable opening to allow access to the interior organs. This cut was generally large enough to allow the use of human hands, either the surgeons or those of a member of the surgical team, as a retractor. Surgical personnel would thus insert their hands through the incision into the abdominal cavity to push and hold organs and other obstructing components away from the surgical objective.

Recently, as a result of the evolution in electronic video technology, a surgical procedure known as laparoscopic surgery has undergone a marked increase in popularity. The laparoscope consists of a long thin rigid tube. Residing at one end of the tube is a viewing lens; at the other is a camera hook up and an eye piece. A small incision in the area of the surgical objective is made and the laparoscope is partially inserted into this incision, viewing lens first. High definition video cameras and monitors are then attached to the camera hook up joint on the part of the laparoscope which remains on the exterior. In this manner, a surgical team can get a clear picture of the affected internal area without resorting to radical, disfiguring surgical incisions to physically open the patient. Numerous other small puncture wounds are then made through the surface of the skin also in the vicinity of the surgical objective. Through these incisions, miniaturized surgical instruments such as scissors, forceps, clamps and scalpels are insertable to perform the surgical procedure. The entire interior procedure is monitored from the exterior through the high definition television monitor. In this manner radical incisions and scarring are avoided while undertaking surgical repair or removal of damaged or diseased organs. Another benefit of laparoscopic surgery is the significantly reduced recovery time, when compared to standard surgical procedures, due to the minuscule size of the scalpel wounds and avoidance of the massive internal traumatization known in standard surgical procedures. Accompanying the reduced recovery time are, of course, greatly reduced costs.

Until recently, laparoscopic surgery was limited to gynecological and arthroscopic procedures. Recently, however, innovative surgeons have been using the procedure to perform cholecystectomy, commonly known as gallbladder removal. A problem encountered by surgeons when performing laparoscopic cholecystectomy is the intrudence of other internal abdominal organs into the surgical objective area i.e. gallbladder area. Abdominal organs such as the stomach, intestine and liver are known to be floppy and to overlap one another. Standard gallbladder surgery of the past, in which a huge incision was made in the patient's abdominal wall, allowed for the insertion of hands into the patient's abdominal cavity to push and hold these floppy organs away from the gallbladder while the surgeon effected the necessary removal. Laparoscopic cholecystectomy, with its minute surgical incisions, does not allow for the insertion of a human hand into the cavity to retract the floppy organs.

There is a need therefore to provide an instrument which can be inserted through a tiny surgical incision in the abdominal wall, to be used during laparoscopic surgery within the abdominal cavity, to push and hold neighboring internal organs away from that organ which is being excised or repaired. For example, during the known procedure of laparoscopic cholecystectomy, a retractor instrument is needed to push and hold neighboring organs away from the diseased gallbladder.

SUMMARY OF THE INVENTION

It is a general object of this invention to provide a retractor device to be used during laparoscopic surgical procedures.

It is an object of this invention to provide a retractor device to be used during laparoscopic surgery within the abdominal cavity.

Another object of the invention is to provide a long thin tube-like instrument suitable for insertion into the abdomen through a tiny incision in the abdomen wall to be used when performing laparoscopic abdominal surgery.

It is a further object of this invention to provide pivotable finger-like protrusions extending from that end of the tube which is inserted into the abdomen to be used as a push and hold means and for establishing means of communication to these protuberances from levers that depend from that end of the tube which remains exterior of the abdomen, said levers to be used in controlling the workings of the push and hold means within the abdomen.

In the accomplishment of these objectives, a retractor device is provided. The device is comprised of a means to do the actual retracting, i.e. pushing and holding internal organs and a means to control the action of the retractor means.

In another embodiment of these objects a long narrow tube-like structure is provided. The tube is generally hollow and open at each end. At one end a plurality of finger-like protuberances are positioned within the tube on the same axial plane as the tube and will extend outwardly from the tube upon movement of the control means at the other end, such as a pair of lever means which depend from the opening. Within the narrow elongated body, comprising a tube, reside the internal mechanism and means for communicating movement of the levers to movement of the finger-like protuberances. In one example the levers are biased apart and manipulation of the levers so as to bring them closer together is communicated to the finger-like protuberances so as to spread them out in a fan type pattern. A release of force on the levers allows the levers to return to their normally apart position. This, in turn, allows the finger-like protuberances to return to their original position, i.e. close together on the same axial plane as the narrow elongated body structure. In this manner the retractor can be inserted into the abdominal cavity through an incision in the abdominal wall or through a sheath which has been placed through an incision in the abdominal wall, and guided to the surgical objective by monitoring the movement of the retractor within the cavity on the laparoscope and its associated high definition television monitor. Once the retractor has been positioned suitably near the organ of interest, the surgeon or a member of the surgical team, by squeezing together the levers depending from that end of the retractor which has not been inserted into the cavity, can cause the finger-like protuberances to spread apart in a fan-like pattern to push and hold surrounding organs away from that organ which is the surgical objective. In this manner abdominal laparoscopic surgery is greatly simplified as the problem caused by floppy, overlapping organs encroaching upon the organ which is the surgical objective has been eliminated.

The above-listed preferred aspects are not intended as limiting. For instance, the device can be constructed with the finger-like protrusions nominally in the opened up fan-like pattern. In this manner, forcing the levers together will cause the protrusions to come together on the same axial plane as the elongated body. The finger-like protuberances can then be inserted into the abdominal cavity while maintaining force on the levers to hold them together. Once near the surgical objective, the levers can be released causing the finger-like protuberances to open up into their normally open fan-like pattern pushing and holding intruding organs out of the way of the surgeon. When used in this manner, the requirement of having a member of the surgical team tend to the retractor levers and hold them together is thus eliminated.

A further embodiment includes the finger-like protrusions arranged in a stacked relationship with respect to each other, so that the protrusions are positioned parallel to each other along a common diametric line with respect to the tubular body. In this embodiment, the finger-like protrusions are at rest substantially within the tubular body, and extend outwardly in a substantially planar fan-like pattern upon movement of the levers. As the levers move, the protrusions extend outwardly in the planar fan-like pattern so that the protrusions remain in position along the common diametric line.

It is contemplated for this embodiment that the lever device for activating the retractor finger-like protrusions be replaced by a syringe-like mechanism in which a pair of finger grips are provided which radially extend from and are secured to the tubular body. A thumb activated push button is attached to the inner rod to control the extension of the finger-like protrusions. The finger grips may be rotatable about the tubular body so that position of the protrusions along the common diametric line in relation to the finger grips may be oriented to suit the needs of the surgical team for that particular operation. Preferably, the diametric line of the protrusions is parallel to the diametric positioning line of the finger grips until altered by the surgical team.

It is also possible to manufacture the device with the levers depending straight out from the elongated body on the same axial plane or have them depend away from the body at some angle, for instance at a 90° angle to the retractor body. It will also be possible to form finger loops in the levers for insertion of the fingers of the member of the surgical team operating the retractor during the laparoscopic surgery. The elongated body structure of the retractor can also be made to be flexible so as to facilitate the positioning of the protruding fingers in close proximity to the area of the surgical objective.

BRIEF DESCRIPTION OF THE DRAWINGS

FIG. 9 illustrates an alternate embodiment of the device shown in FIG. 8 in which the secondary lever is slidably attached to the head;

FIG. 10 illustrates another sheath embodiment of the retractor in which the engagement members normally reside without the sheath in an open position and lever controls are used to close and withdraw the engagement members within the sheath;

FIG. 16 illustrates the retractor having the engagement members positioned parallel to each other along a common diametric line;

DETAILED DESCRIPTION OF THE INVENTION

Figure 1:
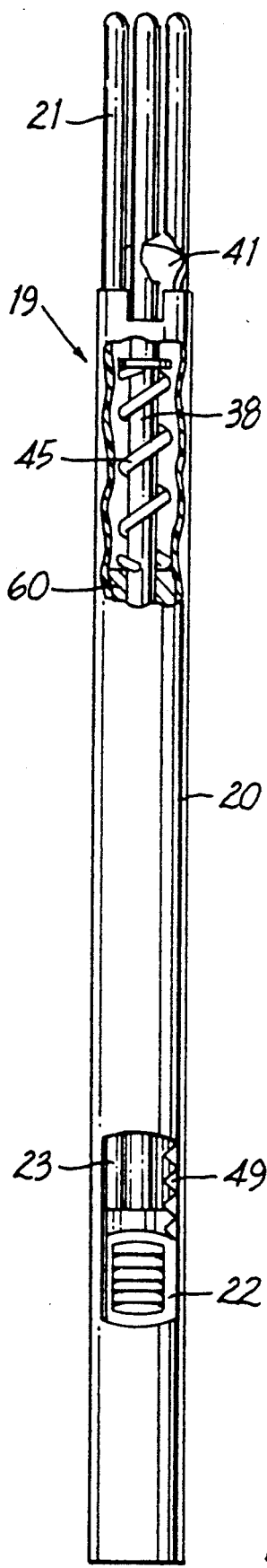
FIG. 1 illustrates the retractor having a slide button control with the engagement members in a closed state.
Figure 2:
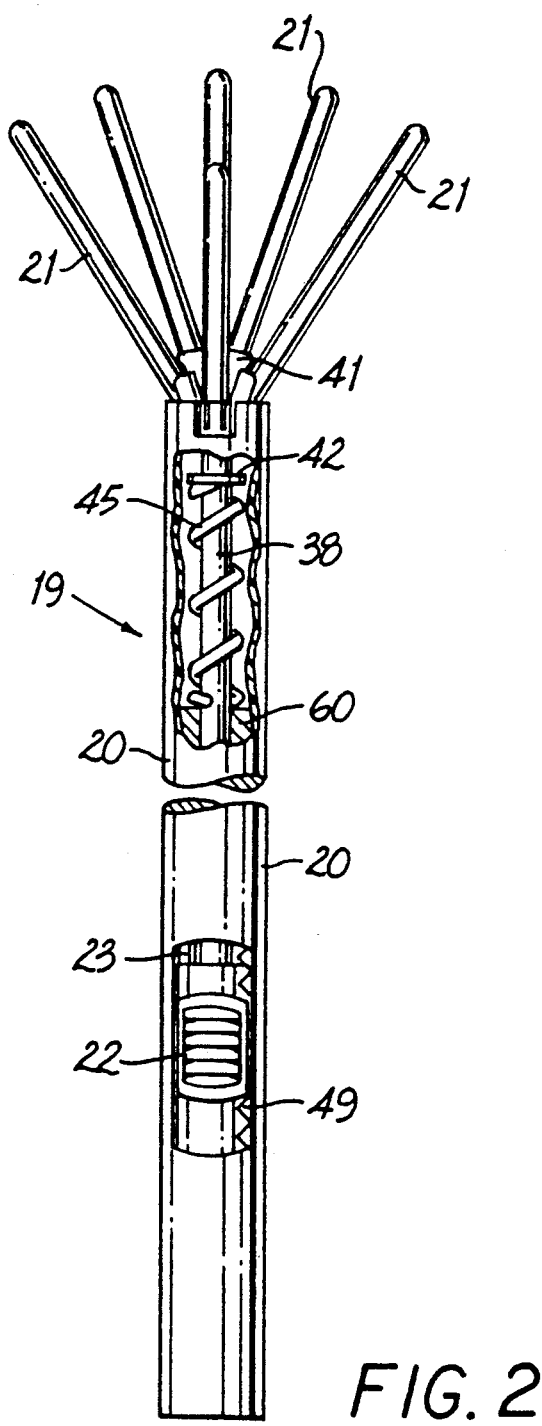
FIG. 2 illustrates the retractor having a slide button control shown with the engagement members in a partially opened state.
Figure 13:
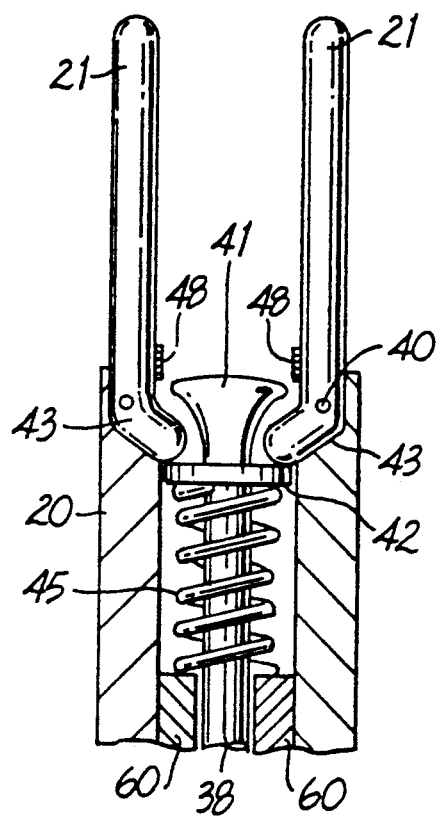
FIG. 13 illustrates a cut-away view of the operation of the engagement members of the embodiments portrayed in FIGS. 1, 2, 3 and 5.

Referring to FIGS. 1 and 13, the retractor 19 is shown with engagement members 27 biased to a closed resting position and control button 22 biased to a set position within slide path 23. In this manner, engagement members 21 and a portion of tube-like body 20 are insertable through a small incision in an abdominal wall. Control button 22 can then be forcibly slid within slide path 23 to effect an opening of engagement members 21 into a fanned-out pattern as shown in FIG. 2. In this manner internal organs can be pushed and held away from that organ which is the surgical objective.

FIG. 13 more clearly depicts the operation of the engagement members 21. The button 22 is fixedly connected to movable shaft 38. Engagement members 21 are pivotally connected to tube-like body 20 by pivot joints 40, so that the outward movement of the engagement members 21 occurs due to pivoting of the members 21 rather than by outward deflection of flexible members, as in the prior art. Movable shaft 38 terminates with knob 41. Disc 42 is fixedly attached to movable shaft 38 at a point just below knob 41. The engagement members 21 have lips 43 that are enclosed between knob 41 and disc 41. Spring 45 circumferentially encompasses movable shaft 38 and is fixedly attached at one end to disc 42. The other end of spring 45 is fixedly attached to inner guide wall 60. Inner guide wall 60 can run any distance through tube-like body 20 but must terminate a sufficient distance below disc 42 to enable the placement of spring 45 between the top of inner guide wall 60 and disc 42.

Operation of engagement members 21 is effected by sliding button 22 which produces a movement of movable shaft 38 towards the engagement members 21. Disc 42 is forced against the pull of spring 45. Disc 42 pushes against lips 43 causing engagement members 21 to rotate about pivots 40 and assume an open position. It can be seen that the farther the movable shaft 38 is moved toward engagement members 21 the greater the rotation of the engagement members 21 about pivots 40, and hence the greater diameter of the open, fanned-out pattern. A cessation of force on control button 22 allows control button 22 to return to its original set position and engagement members 21 to return to their normally closed resting position as shown in FIG. 2. This action is achieved due to the pull of spring 45 upon disc 42, which in the absence of any counter forces, pulls movable shaft 38, disc 42 and knob 41 in a direction opposite engagement members 21. Knob 41 will be forced against lips 43 which will cause reverse rotation of engagement members 21 about pivots 40 to bring engagement members 21 to a closed position in which they occupy the same axial plane as the elongated tube-like body 20. Stop pieces 48 may be placed in the position shown in FIG. 13 to prevent excessive inward rotation of engagement members 21. Stop pieces 48 may alternatively be placed under lips 43.

It is also possible, but not shown in the drawings, to fixedly attach at least one engagement member 21 to knob 41. A structure of this sort would be beneficial in terms of operation of the device since these fixedly attached engagement members would aid in displacement of organs and prevent a displaced organ from jumping over one of the movable engagement members 21 and occupying its position before displacement.

Engagement members 21 can be of any shape as long as their retracting function can be achieved. Preferably engagement members 21 are of cylindrical shape with rounded exposed ends so that soft tissue injury is minimized.

It is also preferred that engagement members 21 are constructed of a substantially rigid material so that bending or deflecting of the engagement members 21 in the open or fanned-out position is limited. While some deflection is considered to avoid damage to the organs, it is preferred that the material of which engagement members 21 be substantially rigid to properly hold the organs in the displaced location. As described above, the fan-like arrangement of engagement members 21, in the extended position, is effected by a pivoting action of members 21 about pivot points 40 as required by the rigid nature of the members, as opposed to the fanning out of the members as in the prior art due to the spring-like flexibility of the prior art engagement members.

Referring to FIGS. 1 and 2, a means to hold or lock the activating button 22 at points within slide path 23 are preferred embodiments and allow for controlling the diameter of the fan-out pattern of engagement members 21 and also for hands-off utilization of the retractor 19. The holding means could be, for example, notches 49 along slide path 23 for physically holding control button 22 at points through its path of travel through slide path 23.

Figure 3:
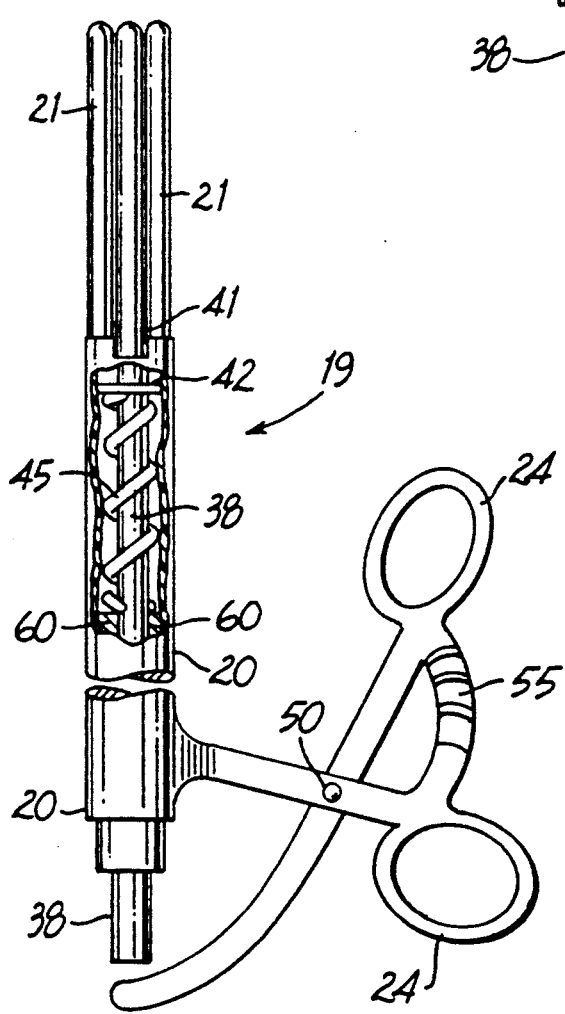
FIG. 3 illustrates the retractor with lever controls and the engagement members in a closed state.

A modification of this embodiment of the device is shown in FIG. 3. Levers 24 are used instead of a button to force movement of movable shaft 38. Levers 24 are pivotally joined at pin 50 with one of the levers making contact with the end of movable shaft 38 opposite engagement members 21. As seen in FIG. 3, movable shaft 38 is shown in this embodiment to extend outward from tube-like body 20. Operation of engagement members 21 upon forcing of movable shaft in the direction of engagement members 21 by squeezing of levers 24 is identical to that previously described when referencing FIG. 13 and such description is incorporated by reference herein.

Figure 4:
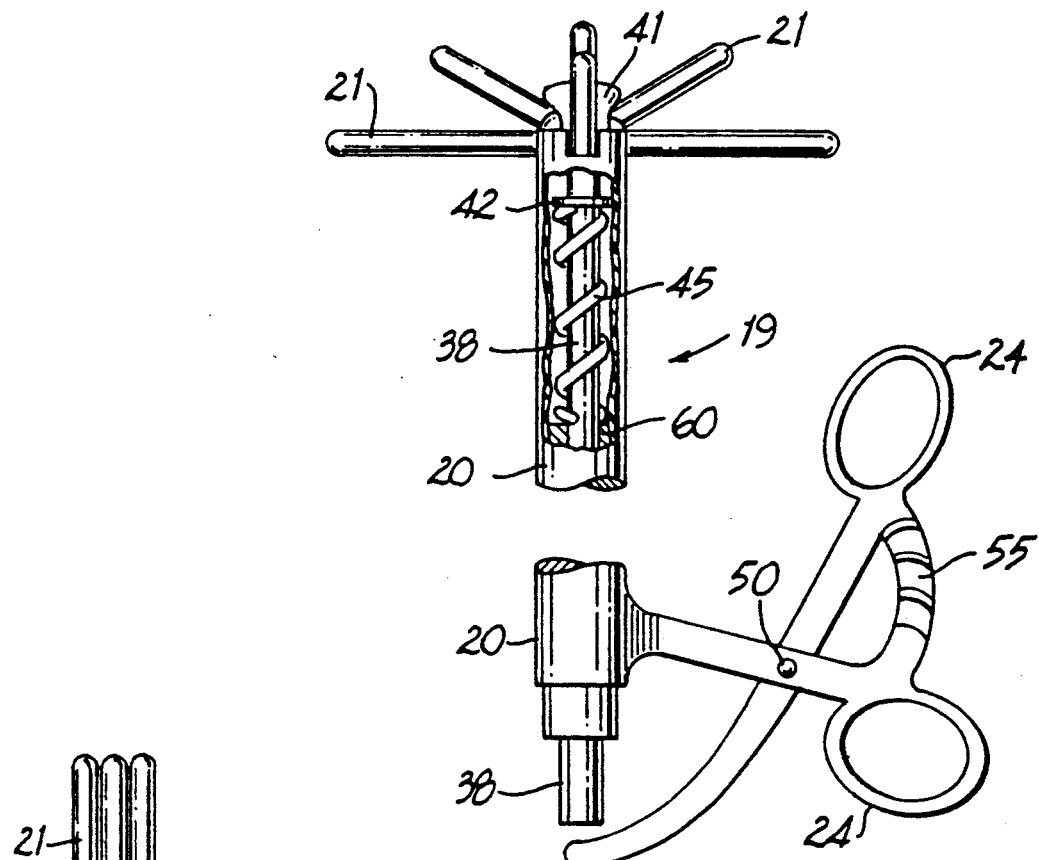
FIG. 4 illustrates an alternate embodiment of FIG. 3 in which the engagement members are in a normally opened state.
Figure 14:
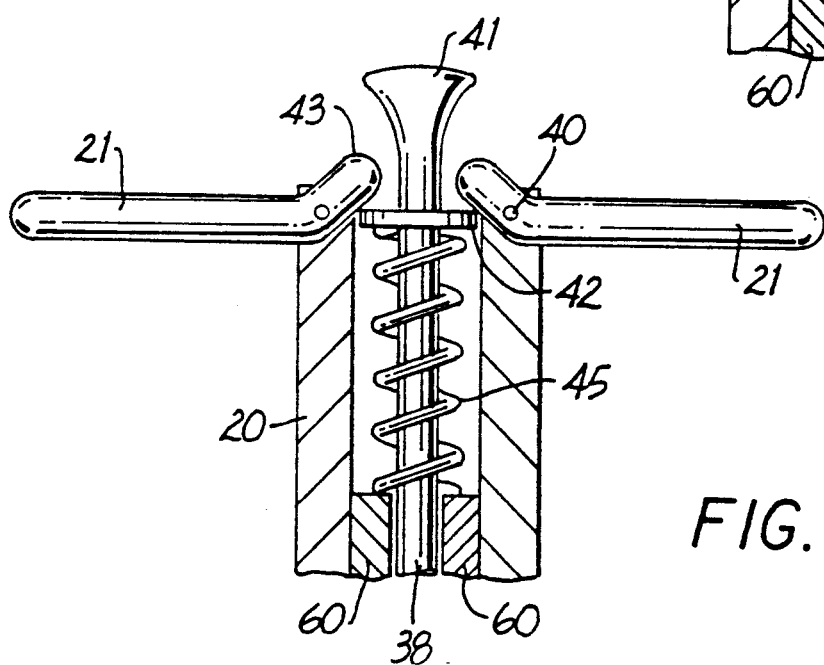
FIG. 14 illustrates a cut-away view of the operation of the engagement members of the embodiments portrayed in FIG. 4.

Referring to FIGS. 4 and 14, another embodiment using levers 24 is shown. In this embodiment engagement members 21 are normally open. The normally open state results from spring 45, which is affixed at the top of the fixed inner guide wall 60 and disc 42, exerting a push force against disc 42 in the absence of any other forces. Disc 42, which is fixedly attached to movable shaft 38 impacts upon lips 43 to cause outward rotation of engagement members 21 about pivots 40. In order to close engagement members 21, it is necessary to squeeze levers 24 together. This pulls movable shaft 38 back towards the end of the device opposite engagement members 21 due to the connection with one of levers 24 with movable shaft 38 at connection 51. Drawing movable shaft 38 back towards levers 24 causes knob 41 to impact upon lips 43 while compressing spring 45 to force rotation of engagement members 21 about pivots 40 in a direction that will cause engagement members 21 to close together along the same axial plane as tube-like body 20. Releasing force on levers 24 causes spring 45 to expand which in turn presses disc 42 on the underside of lips 43 causing engagement members 21 to rotate outward into their normally opened, fanned-out state.

Figure 5:
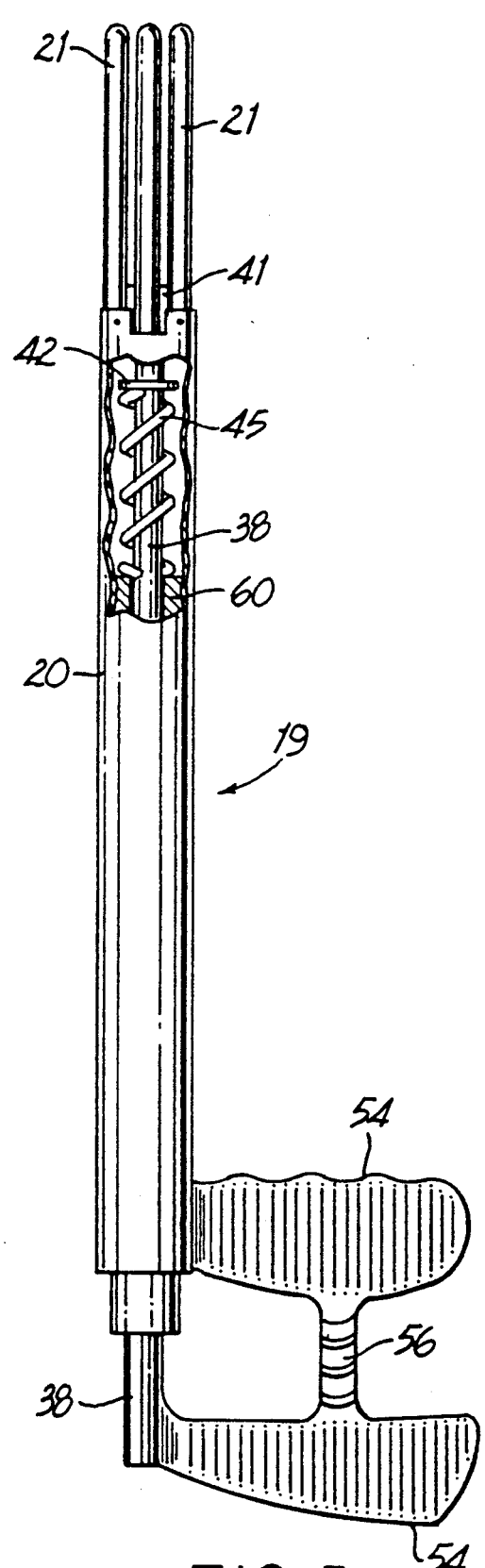
FIG. 5 illustrates yet another embodiment of FIG. 3 with handle controls.

Another embodiment of the device is shown in FIG. 5 in which handles 54, one attached to the elongated tube-like body 20 at the end away from engagement members 21, the other attached to the end of movable shaft 38 at the end opposite engagement members 21, are utilized for control. By gripping and squeezing handles 54, movable shaft 38 is moved in the direction towards engagement members 21 causing an opening of engagement members 21 in the manner previously described when referring to FIG. 13.

In any of the aforementioned embodiments which use levers 24 or handles 54, it is preferable to include means to hold the levers 24 or handles 54 at various points in their movement towards one another. This could be accomplished, for example, by an adjustable clip 55 to hold the levers 24 or handles 54 together, or by equipping each lever 24 or handle 54 with a horizontal appendage 56 with backwards facing teeth for interlocking the levers 24 or handles 54.

Figure 6:
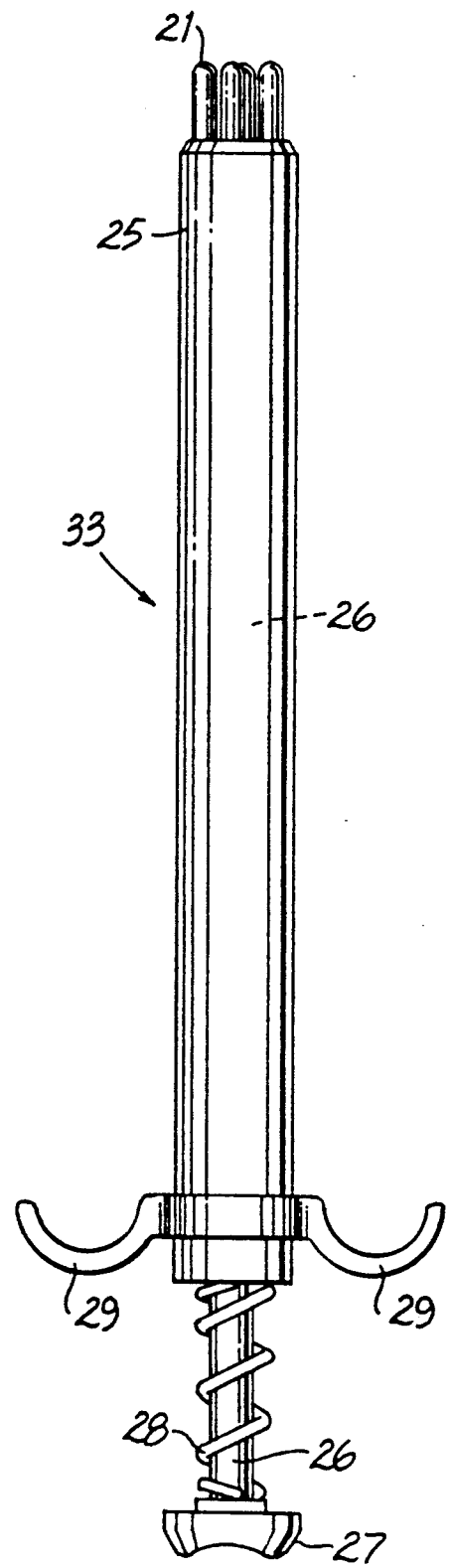
FIG. 6 illustrates the alternate sheath embodiment of the retractor showing the engagement members withdrawn into the sheath.
Figure 7:
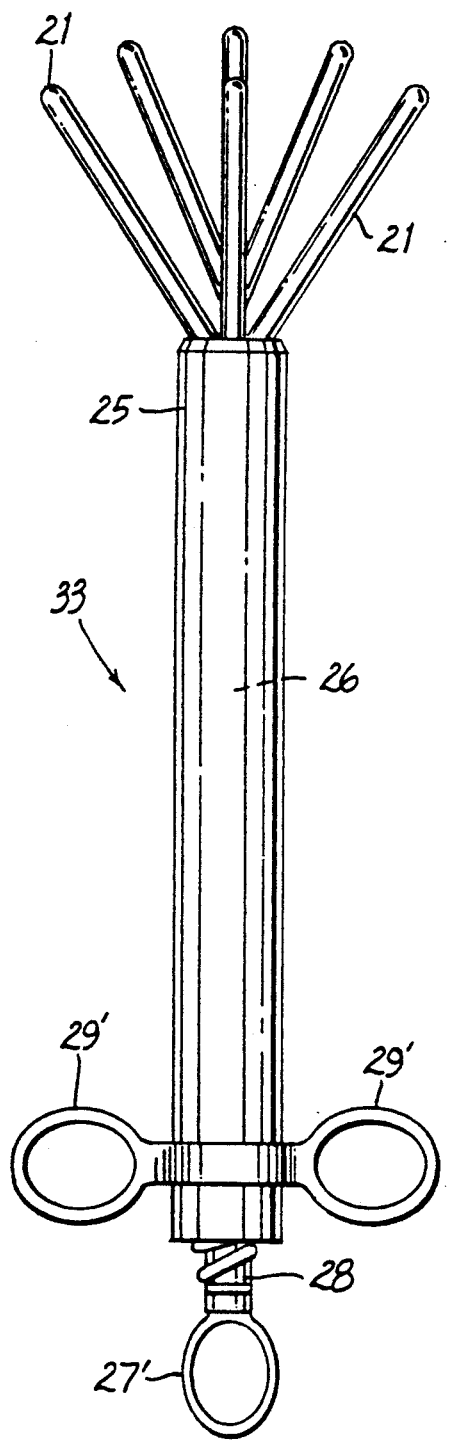
FIG. 7 illustrates the retractor of FIG. 6 showing the head depressed and the engagement members outside of the sheath and opened.

Referring to FIG. 6, sheath 25 is shown. Residing within sheath 25 is rod 26. Rod 26 is slidably mounted within sheath 25 so that force on rod head 27 against bias force propels the rod head 27 towards sheath 25 allowing engagement members 21 to exit from within sheath 25. The absence of the containing action caused by sheath 25 on engagement members 21 when engagement members 21 are without sheath 25 allows engagement members 21 to expand into an opened-up fanned-out pattern. This occurrence is demonstrated by FIG. 7. In this instance the bias is shown to be a spring 28 wrapped circumferentially around rod 26 just below rod head 27', shown in this instance as a loop, and exterior to sheath 25. This is not limiting a the spring could conceivably be located within the sheath or some other type of bias could be used. Also shown by FIGS. 6 and 7 are flange members 29 and 29' in the form of partial or complete loops mounted on the exterior of sheath 25. Flange members 29 and 29' facilitate operation of the device 33 by providing the user with means to grasp the device 33 such as with the middle finger and ring finger while applying force, such as with the thumb, to rod head 27 or 27' to force exit and expansion of engagement members 21.

Figure 8:
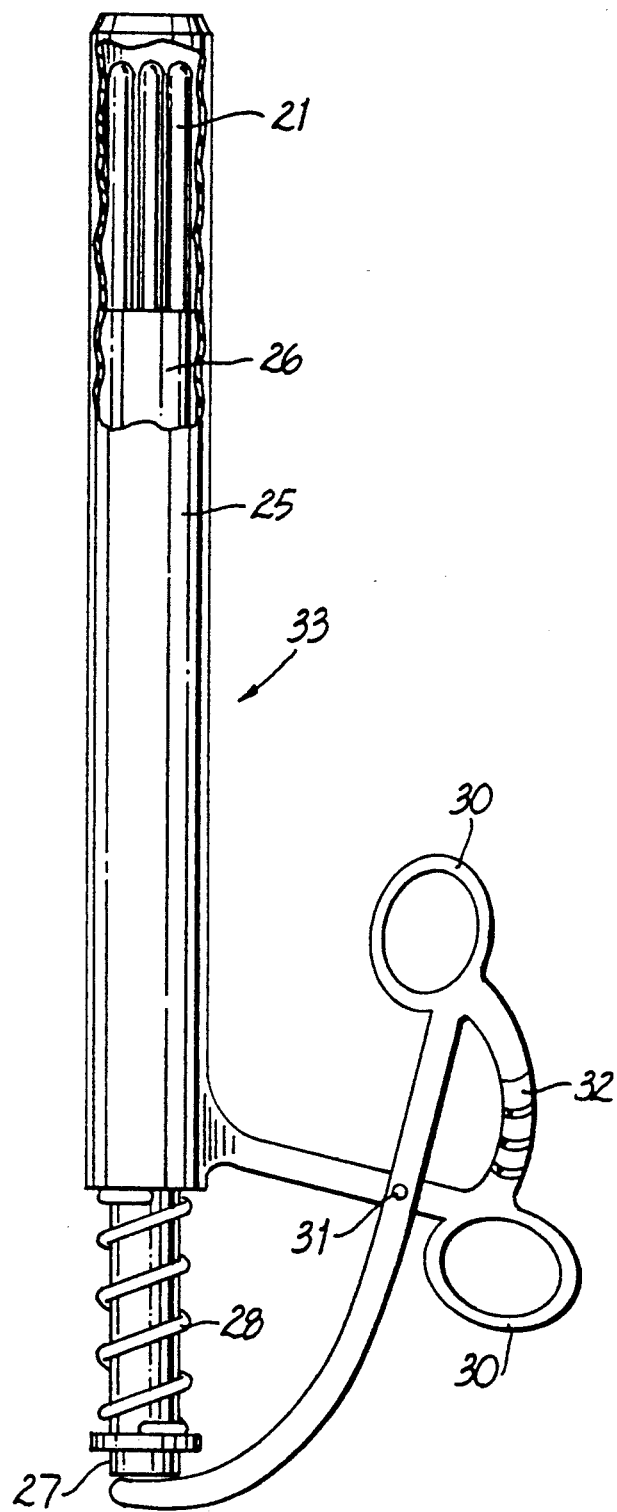
FIG. 8 illustrates a sheath embodiment of the retractor in which levers are used to exert force on the head.

FIGS. 8 and 9 are alternate embodiments of the sheath type mechanism disclosed in FIGS. 6 and 7 which further provide levers 30 for exerting the necessary force on rod head 27 to effectuate action of engagement members 21. In the embodiment as shown in FIG. 8 one lever is fixedly attached to sheath 25 while the other lever imparts force on rod head 27 but is not physically attached to rod head 27. FIG. 9 shows the same retractor 33 but with a lever 30 slidably attached to rod head 27. In each shown embodiment of the retractor 33 with levers 30, the levers 30 are connected to one another at pin 31. Biasing means is shown in both figures to be accomplished by use of spring 28 located circumferentially on rod 25 adjacent to rod head 27 and exterior to sheath 25. A means to hold the levers 30 in numerous closed or partially closed positions to fixedly secure the rod 26 within the sheath 25 at numerous positions to effect the fan out diameter of engagement members 21 is shown as toothed clip 32.

FIG. 10 is an alternate embodiment of the sheath type retractor 33 wherein the normal position, i.e. with no forces being exerted, of the components of the retractor 33 are as shown. The rod head 27 is biased, for example, by spring 28 to a position against sheath 25 so that engagement members 21 normally reside without sheath 25 and display an opened fanned out pattern. Force exerted on levers 30 in the form of squeezing the bottom of the levers 30 together acts to pull rod head 27 away from sheath 25 forcing engagement members 21 into a closed position as they are withdrawn within sheath 25. As with any of the other embodiments of the retractor various bias means instead of spring 28 can be utilized as well as varying means to hold rod 26 within sheath 25 at different lateral locations to control the diameter of the spread of engagement members 21.

Figure 11:
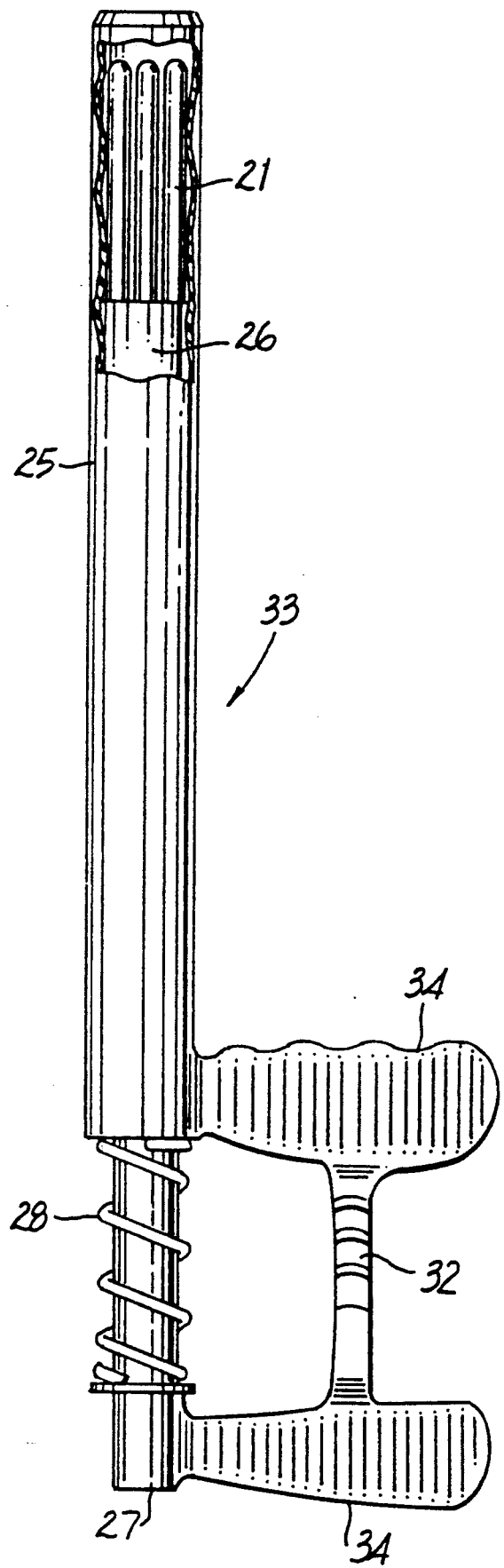
FIG. 11 illustrates a sheath embodiment of the invention in which fixed handles are used to force out the engagement members from within the sheath.

FIG. 11 is yet another embodiment of the sheath type embodiment of retractor 33 in which handles 34 control engagement members 21. For proper use of the device as shown in FIG. 11, the user can grasp the handles 34 and squeeze them together against the force of bias which in this instance is shown to be spring 28, to force rod 26 towards the open end of sheath 25 so that engagement members 21 can exit from within sheath 25 and assume an open fanned-out pattern.

Figure 12:
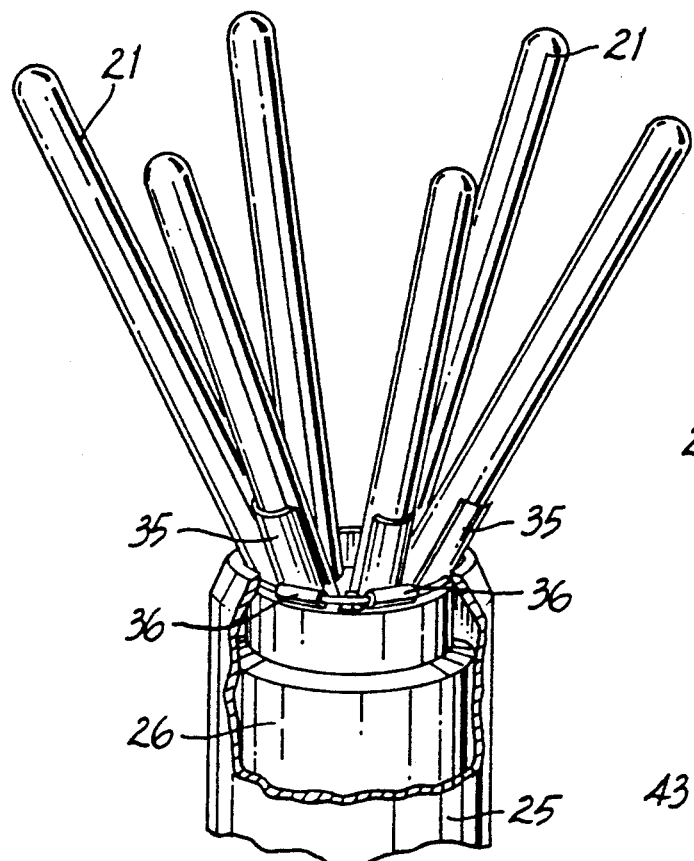
FIG. 12 illustrates a detailed view showing one method of biasing the engagement members open.

FIG. 12 is a close-up view of one of the mechanisms which may be utilized to effectuate an opening of engagement members 21 when they are forced out of sheath 25. Engagement members 21 are shown to be attached to the end of rod 26 by pivot joints 36. When forced without the confining boundaries of sheath 25, spring fan outs 35 pull back on engagement members 21 to pivot them into an opened, fanned-out pattern. As can be seen, the amount by which engagement members 21 are forced without sheath 25 will directly affect the diameter of the fanned-out pattern caused by spring fan outs 35 acting in conjunction with pivot joints 36.

Figure 15:
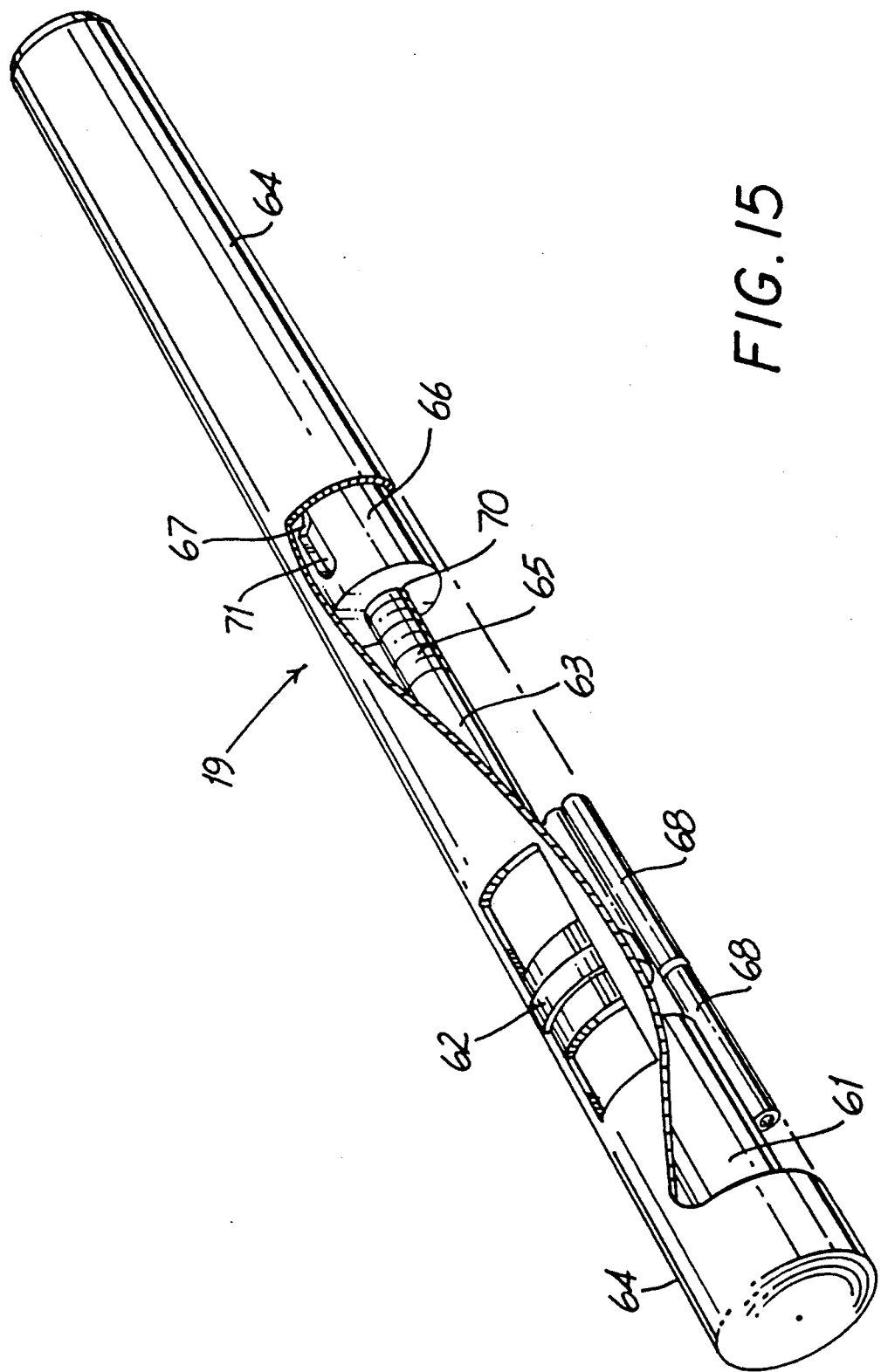
FIG. 15 illustrates the retractor having an electromechanical control.

Recognizing that lateral displacement of a movable shaft or rod is essential for operation of any embodiment of the device, it is possible to utilize an electromechanical device, such as a motor, to achieve such lateral displacement. FIG. 15 is one example of how a motor might be used to produce lateral displacement of a shaft or rod.

Within retractor 19 and casing 64 is found reversible motor 61. Reversible motors of this design are known in the art and require no further explanation. Reversible motor 61 is shown to be controlled by slide switch 62. Slide switch 62 can be of the known type having a center-off position. Switch 62 can be displaced in either direction above or below the center-off position.

Displacement of switch 62 in one direction causes rotation of threaded shaft 63 in one rotational direction; displacement of switch 62 in the other direction causes opposite rotation of threaded shift 63.

Threaded shaft 63, has threads 65 which engage threads 70 of hollow cylinder 66. Rotation of threaded shaft 63 laterally displaces hollow cylinder 66 due to the engagement of threads 65 and 70. It can be seen that lateral displacement of hollow cylinder 66 can occur in either direction resulting from the ability to reverse the rotational direction of threaded shaft 63.

In order to prevent rotation of hollow cylinder 66, groove 71 is cut through the wall of hollow cylinder 66. Pegs 67 are fixedly attached to the inner wall of casing 64 and protrude inward through groove 71. In this manner, pegs 67 prevent rotation of hollow cylinder 66 while allowing lateral displacement of hollow cylinder 66.

The retractor 19 shown and described in FIG. 15 is preferably a portable self-contained unit. In furtherance of this objective, reversible motor 61 receives electrical power from on-board batteries 68.

The control means disclosed in FIG. 15 would suitably replace any of the control mechanisms disclosed in FIGS. 1-11. The control means of FIG. 15 would control engagement members 21 by virtue of lateral displacement of hollow cylinder 66 by the methods as shown and described in FIGS. 12-14. With respect to FIGS. 13 and 14, spring 45 would not be necessary and could be eliminated when the control mechanism shown in FIG. 15 and described above is utilized.

A preferred embodiment of the retractor device is illustrated in FIGS. 16-19. Retractor 80 consists essentially of tubular body 82 through which rod member 84 passes. Rod member 84 terminates in a mechanism as described above for pivotally securing engagement members 88 to rod member 84. Rod member 84 is biased as shown in the retracted position by biasing spring 86. Engagement members 88 are shown to be partially extending from body 82, but may, of course, be fully within body 82 when retractor 80 is at rest. Finger grips 90 are provided, and rod member 84 terminates in thumb button 92. Finger grips 90 are secured to body 82 as shown, but it is contemplated that grips 90 are rotatably secured to body 82 to allow the surgical team member operating retractor 80 to better orient the device if necessary.

Figure 18:
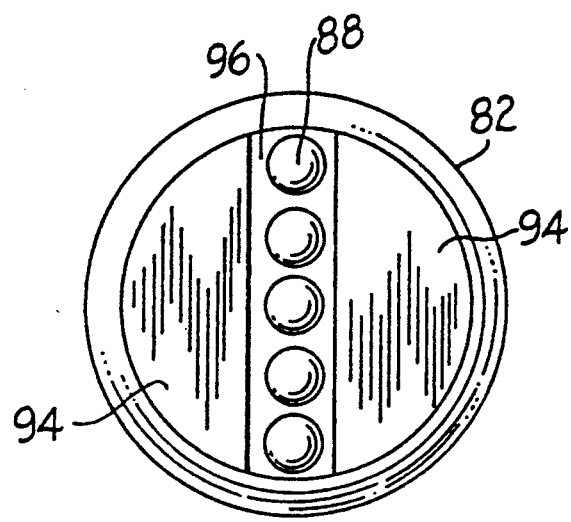
FIG. 18 illustrates the retractor of FIG. 16 taken along lines 18—18.
Figure 19:
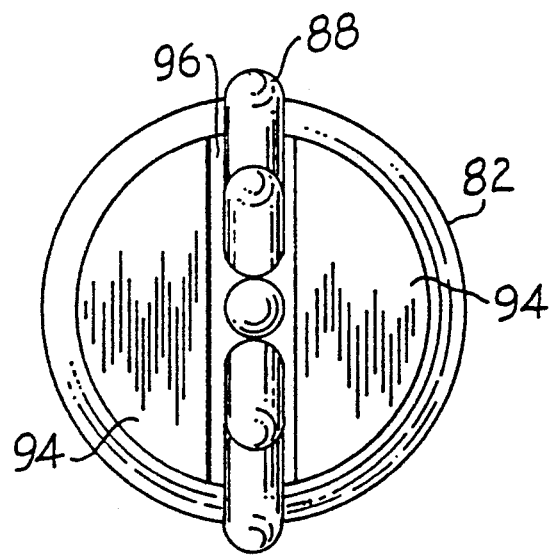
FIG. 19 illustrates the retractor of FIG. 17 taken along lines 19—19.

Engagement members 88 are positioned in a stacked relation along the same diametric line in relation to body 82, as best seen in FIG. 18. When members 88 are retracted as shown in FIG. 18, they are positioned parallel to each other and substantially parallel to the longitudinal axis of body 82. Preferably, land portions 94 are provided to limit any radial deflection of members 88 during use when they are extended outside body 82. Land portions 94 may be eliminated, so that opening 96 is bounded only by body 82.

Figure 17:
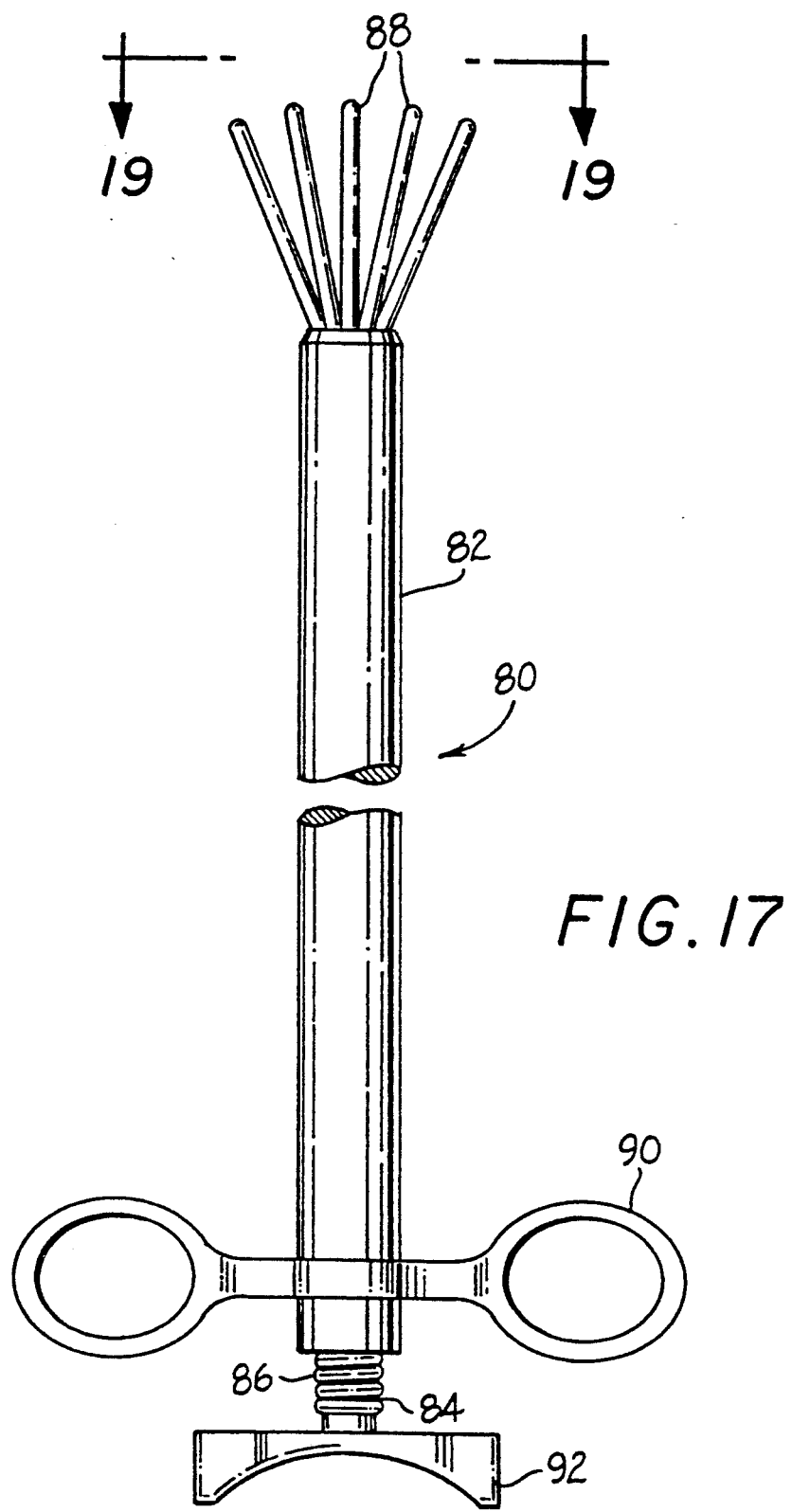
FIG. 17 illustrates the retractor of FIG. 16 with the engagement members extended in a substantially planar fan-like arrangement.

As best seen in FIG. 17, in use, finger grips 90 are grasped by the user and thumb button 92 is pushed to the position shown against the biasing force of spring 86. Rod member 84 extends into body 82, and engagement members 88 extend outwardly from body 82. Members 88 pivot in the manner described above, and remain aligned in substantially the same diametric line so that they assume a substantially planar fan-like arrangement. This can best be seen in FIG. 19, where the fan-like arrangement is substantially planar. As thumb button 92 is released, spring 86 biases rod 84 to return to the position shown in FIG. 16, and engagement members 88 pivot and return to their retracted position.

Although a few particular embodiments of the invention have been shown and described, various forms and embodiments of this device are possible within the scope of the invention claimed. Biasing means can be altered in both form, such as spring, and position on the device, such as mounted on the rod or perhaps mounted on the lever means. The fan out actuation of the engagement members can be accomplished by the methods as shown or perhaps by forming the retractor means so that they have a tendency to fan out when the constraining action of the sheath is removed. Various methods of positioning the rod within the sheath or, relatedly, holding the lever means in various positions with respect to one another, are possible and will be evident to those skilled in the art. Further modification of the device within the scope of the invention will also be apparent to those skilled in the art in view of this disclosure. Accordingly, reference should be made to the appended claims rather than the foregoing specification in assessing the scope of the invention in which exclusive rights are claimed.

What is claimed is:

1. A retractor to be inserted into an abdominal cavity for displacement of organs within the cavity comprising:
   an elongated device body having a first length and being insertable from a first end into an abdomen;
   engagement means for displacing the organs, said engagement means being pivotably disposed in relation to said device body at said first end and having a second length less than said first length of said elongated device body; and
   means for controlling said engagement means, said control means being operatively connected to said engagement means through said device body to pivot said engagement means outwardly in relation to said device body;
   said control means being operable to pivot said engagement means outwardly from a retracted position to at least one intermediate position, said control means being further operable to pivot said engagement means outwardly from said at least one intermediate position to a fully extended position;
   whereby said control means can be manipulated outside said abdomen at a second end of said elongated device body to control said engagement means.

2. The retractor recited in claim 1 further comprising an electric motor and power source, said motor being operatively associated with said control means.

3. The retractor recited in claim 1 wherein the body is flexible.

4. The retractor recited in claim 1 wherein said engagement means are comprised of a plurality of finger-like protuberances being essentially cylindrically shaped having rounded outer-most ends.

5. A retractor to be inserted into an abdominal cavity for displacement of organs within the cavity comprising:
   a device being at least partially into an abdomen having engagement means for accomplishing the displacement and means for controlling said engagement means, said control means including first and second lever arms depending from said device and biasing means, at least one said lever arm being movable through a path of movement;
   wherein said control means are biased to a set position and said engagement means are biased to a resting position and wherein forcible movement of said control means causes said engagement means to depart from said resting position and wherein terminating said force on said control means allows said control means to return to said set position and said engagement means to return to said resting position.

6. The retractor as recited in claim 5 wherein at least one spring means is used for biasing.

7. The retractor recited in claim 5 wherein said first and second lever arms are biased to a set position in which said levers are apart defining an angle and said engagement means are biased to a resting position in which they are closed together substantially occupying the same axial plane as the device whereby forcing said first and second lever arms against said bias moving said arms together opens said engagement means into a substantially fanned-out shape.

8. The retractor recited in claim 5 wherein said first and second lever arms are biased to a set position in which said levers are apart defining an angle and said engagement means are biased to a resting position of an open fan-like pattern whereby forcing said first and second lever arms against said bias moving said arms together brings said engagement means to a closed together position substantially occupying the same axial plane as the device.

9. The retractor recited in claim 5 wherein moving at least one said lever arm through said path of movement controls movement of said engagement means in a substantially linear manner whereby the distance at least one said lever arm is moved substantially correlates directly to movement of said engagement means.

10. The retractor recited in claim 5 wherein at least one said lever arm is pivotally connected to said device.

11. The retractor recited in claim 5 wherein said lever arms depend perpendicularly from said device with at least one said lever arm slidably mounted to said device.

12. The retractor recited in claim 5 further comprising means to hold at least one said lever arm in at least one position along its path of movement.

13. The retractor recited in claim 5 wherein said first and second lever arms have at least one loop formed therein for insertion of at least one finger.

14. A retractor to be inserted into an abdominal cavity for displacement of organs within the cavity comprising:
a device being at least partially insertable into an abdomen having engagement means for accomplishing the displacement and means for controlling said engagement means, said control means including first and second lever arms depending from said device and biasing means, at least one said lever arm being movable through a path of movement, said control means being biased to a set position and said engagement means being biased to a resting position wherein movement of said control means from said jet position causes movement of said engagement means from said resting position and wherein movement of said control means toward said jet position causes movement of said engagement means towards said resting position.

15. A retractor to be inserted into an abdominal cavity for displacement of organs within the cavity comprising:
a device being at least partially insertable into an abdomen having an engagement means for accomplishing the displacement and means for controlling said engagement means, said control means including a slide button slidably mounted in a slide-path on said device and biasing means;
wherein said control means are biased to a set position and said engagement means are biased to a resting position and wherein forcible movement of said control means causes said engagement means to depart from said resting position and wherein terminating said force on said control means allows said control means to return to said set position and said engagement means to return to said resting position.

16. The retractor recited in claim 15 wherein sliding of said button controls movement of said engagement means is a substantially linear manner whereby the distance said button is slid substantially correlates directly to movement of said engagement means.

17. The retractor means recited in claim 15 further comprising means to hold the slidable button at at least one point along the slide path.

18. A retractor to be inserted into an abdominal cavity for displacement of organs within the cavity comprising:
an elongated hollow tube-like body defining a sheath, said sheath having front and rear ends;
a rod slidably mounted within said sheath having two ends, a primary end defining a head and protruding from the rear end of said sheath and a secondary end providing engagement means normally residing within said sheath, said engagement means being biased to fan-out when slid outside of said sheath;
a mechanism forcing said rod towards the rear of said sheath whereby the engagement means are forced to a closed position and held within said sheath whereby a force exerted on said head of said rod against the force of said mechanism slides the rod towards the front end of said sheath allowing said engagement means to exit from within said sheath assuming a fanned-out pattern.

19. The retractor recited in claim 18 wherein the further said engagement means are slid out of the sheath the greater the diameter of the fanned-out pattern, limited by the length of the engagement means.

20. The retractor recited in claim 18 further comprising at least one flange member fixedly attached to the sheath substantially at the rear end of said sheath.

21. The retractor recited in claim 20 wherein the at least one flange member forms the shape of at least a partial loop for resting of at least one finger therein.

22. The retractor recited in claim 18, further comprising means to fixedly secure the rod within the sheath at at least one point for holding the fan-out diameter of the engagement means in a fixed position.

23. The retractor recited in claim 18, wherein said engagement means are comprised of a plurality of finger-like protuberances being essentially cylindrically shaped having rounded outer-most ends.

24. The retractor recited in claim 18 further comprising primary lever means having a top and a bottom fixedly attached at said top to said sheath substantially at said rear end of said sheath, secondary lever means having a top and a bottom, pivotally connected to said primary lever means, the top of said secondary lever means communicating with said head of said rod whereby squeezing the primary and secondary lever means together at their bottoms causes the secondary lever means to travel in a bottom radial path and causes force to be exerted on the head of said rod against said mechanism.

25. The retractor recited in claim 24 further comprising holding means to secure the secondary lever means in at least one position along its radial path.

26. The retractor recited in claim 24 having at least one loop formed within said lever means for insertion of at least one finger therein.

27. The retractor recited in claim 24 wherein the top of said secondary lever means is pivotally connected to the head of said rod.

28. The retractor recited in claim 24 wherein the top of said secondary lever means is slidably connected to the head of said rod.

29. The retractor recited in claim 24 wherein said mechanism forces the rod towards the front of the sheath whereby the head is seated against the rear of the sheath and said engagement means normally reside outside the sheath in a fully opened fanned-out pattern and said secondary lever is fixedly attached at its top to the head of said rod and is pivotally connected to said primary lever whereby squeezing the primary and secondary lever means together at their said bottoms pulls the rod towards the rear of the sheath against the force of the mechanism, forcing the engagement means into a closed together position and withdrawing them within said sheath.

30. The retractor recited in claim 29 further comprising holding means to secure the secondary lever means in at least one position along its radial path.

31. The retractor recited in claim 29 having at least one loop formed within said lever means for insertion of at least one finger therein.

32. The retractor recited in claim 18 wherein the mechanism is comprised of spring means.

33. The retractor recited in claim 18 wherein the device is flexible.

34. A retractor to be inserted into an abdominal cavity for displacement of organs within the cavity comprising:
   an elongated hollow tube-like body defining a sheath, said sheath having front and rear ends;
   a primary handle depending from said sheath, located substantially at the rear of said sheath;
   a rod slidably mounted within said sheath having two ends, a primary end defining a head and protruding from the rear end of said sheath, and a secondary end defining engagement means normally residing within said sheath, said engagement means being biased to fan-out when slid outside of said sheath;
   a secondary handle depending from the head of said rod;
   a mechanism forcing said rod towards the rear of said sheath whereby the engagement means are forced to a closed position and held within said sheath whereby squeezing the handles together forces the rod toward the front end of said sheath allowing said engagement means to exit from within said sheath assuming a fanned-out pattern.

35. The retractor as recited in claim 34 wherein the further said engagement means are slid out of the sheath the larger the diameter of the fanned out pattern, limited by the length of the engagement means.

36. The retractor as recited in claim 34 further comprising holding means for holding the handles in at least one set position.

37. The retractor as recited in claim 34 wherein said engagement means are comprised of a plurality of finger-like protuberances being essentially cylindrically shaped having rounded outer-most ends.

38. The retractor as recited in claim 34 wherein the mechanism is comprised of spring means.

39. The retractor recited in claim 34 wherein the device is flexible.

40. A laparoscopic retractor device for displacing tissue and organs within an abdominal cavity, comprising:
   an elongated tubular body member having an opening at a first end,
   elongated rod means positioned coaxially within said body member,
   a plurality of finger members normally at least partially residing within said body member and being pivotally secured to said rod means at a first end of said rod means adjacent said first end of said body member,
   an activating mechanism positioned at a second end of said body member and said rod means and cooperatingly engaged with said body member and said rod means to effect movement of said finger members,
   wherein movement of said activating mechanism from a rest position in a first direction to a set position extends said finger members outside said body member, said finger members pivoting outwardly in a fan-like pattern, and further wherein movement of said activating mechanism from said set position in a second direction to said rest position retracts said finger members into said opening, said finger members pivoting inwardly to retract into said body member.

41. A retractor device according to claim 40, wherein said finger members are rigid and cylindrically shaped, said finger members terminating in a rounded spherical end.

42. A retractor device according to claim 40, wherein said rod means comprises a rod member and said activating mechanism is adapted to effect reciprocating movement of said rod member within said body member.

43. A retractor device according to claim 42, wherein movement of said activating mechanism in said first direction moves said rod member through said body member towards said first end, and movement of said activating mechanism in said second direction moves said rod member into said body member.

44. A retractor device according to claim 40, wherein said finger members are pivotally connected to said body member, such that movement of said rod member pivots said finger members outwardly.

45. A retractor device according to claim 40, wherein said rod member is biased towards said rest position by a spring.

46. A retractor device according to claim 41, wherein said finger members are arranged parallel to each other and disposed along a common diametric line in said rest position, such that movement of said rod means extends said finger members in a substantially planar fan-like pattern.

47. A retractor device according to claim 40, wherein said activating mechanism comprises a pair of scissor-like handle members, a first handle member being connected to said body member and a second handle member being connected to said rod member.

48. A retractor device according to claim 40, wherein said activating mechanism comprises a pair of finger grips attached to said body member and a push button attached to an end of said rod member.

49. A retractor device according to claim 48, wherein said finger grips are rotatable about said body member.

50. A laparoscopic retractor device for displacing tissue and organs within an abdominal cavity, comprising:
   an elongated tubular body member having an opening at a distal end;
   elongated rod means positioned coaxially within said body member;
   means for displacing said tissue and organs pivotably secured to said rod means at a distal end adjacent said opening of said body member and normally at least partially residing within said body member; and
   means for reciprocatingly moving said rod means within said body member positioned at a proximal end of said rod means and said body member;
   wherein movement of said moving means from a rest position in a first direction to a set position extends said displacing means outside said body member such that said displacing means pivot outwardly in a fan-like pattern, and further wherein movement of said moving means in a second direction from said set position to said rest position retracts said displacing means into said body member, such that said displacing means pivot inwardly to retract into said body member.

51. A retractor device according to claim 50 wherein said displacing means comprises a plurality of rigid finger members arranged on a common diametric line in said rest position, such that said finger members pivot outwardly in a set position in a substantially planar fan-like pattern.

52. A retractor device according to claim 51 wherein said finger members are pivotably connected to said rod member at individual pivot hinges, such that each finger member pivots outwardly at said hinge.

53. A retractor device according to claim 52, wherein said finger members are constructed of a rigid material, such that said finger members resist flexing during displacement of said tissue and organs.

54. A retractor device according to claim 50 wherein said rod means comprises a rod member and said moving means is adapted to effect reciprocating movement of said rod member within said body member.

55. A retractor device according to claim 54 wherein movement of said moving means in said first direction moves said rod member through said body member towards said first end, and movement of said moving means in said second direction moves said rod member into said body member.

56. A retractor device according to claim 50 wherein said finger members are pivotally connected to said body member, such that movement of said rod member pivots said finger members outwardly.

57. A retractor device according to claim 50 wherein said moving means comprises a pair of scissor-like handle members, a first handle member being connected to said body member and a second handle member being connected to said rod member.

58. A retractor device according to claim 50 wherein said moving means comprises a pair of finger grips attached to said body member and a push button attached to an end of said rod member.

59. A retractor device according to claim 58 wherein said finger grips are rotatable about said body member.

60. A laparoscopic retractor to be inserted into an abdominal cavity for displacement of organs within the cavity comprising:
a body portion insertable at a first end into an abdomen, said first body portion including a tubular member and a rod member reciprocatingly disposed within said tubular member;
engagement means for displacing the organs, said engagement means being at least partially reciprocatingly retractable and extendable in relation to said body portion, said engagement means further being pivotably disposed in relation to said body portion at said first end; and
means for controlling said engagement means, said control means being positioned at a second end of said body portion and being operatively connected to said rod member for reciprocatingly controlling said engagement means through said body portion to pivot said engagement means outwardly in relation to said device body;
whereby said control means can be manipulated outside said abdomen to reciprocatingly control said engagement means.

61. The retractor recited in claim 60 wherein said control means comprises a pair of scissor-like handle members, a first handle member being connected to said body portion and a second handle member being connected to said rod member.

62. The retractor recited in claim 60 wherein said control means comprise a pair of finger grips attached to said body portion and a push button attached to an end of said rod member.

63. The retractor recited in claim 60, wherein said control means is operable to pivot said engagement means outwardly from a retracted position to at least one intermediate position, said control means being further operable to pivot said engagement means outwardly from said at least one intermediate position to a fully extended position.

64. A retractor to be inserted into an abdominal cavity for displacement of organs within the cavity comprising:
an elongated device body insertable from a first end into an abdomen;
engagement means for displacing the organs, said engagement means being pivotably disposed in relation to said device body at said first end; and
means for controlling said engagement means, said control means being linearly movable in relation to said device body and operatively connected to said engagement means through said device body to pivot said engagement means outwardly in relation to said device body;
wherein by said control means can be manipulated outside said abdomen at a second end of said elongated device body to control said engagement means.

65. A retractor to be inserted into an abdominal cavity for displacement of organs with the cavity comprising:
a device body having a distal end insertable into an abdomen, said device body having a first cross-sectional surface area;
engagement means including at least two members for displacing the organs, said engagement means being pivotably disposed in relation to said device body so as to be movable from a first position to a second position; and
means for controlling said engagement means, said control means being operatively connected to said engagement means through said device body to pivot said engagement means outwardly in relation to said device body from said first position to said second position, said control means being manipulable from outside said abdomen to control said engagement means;
wherein said at least two members are dimensioned so as to have a second cross-sectional surface area which is less than or equal to said first cross-sectional surface area of said device body when said engagement means is in said first position, and further having a third cross-sectional surface area which is greater than said first cross-sectional surface area of said device body when said engagement means is in said second position.

66. The retractor recited in claim 65, wherein said control means comprises a pair of scissor-like handle members.

67. The retractor recited in claim 65, wherein said control means comprises a pair of finger grips and a push button mechanism.

68. The retractor recited in claim 65, wherein said control means is operable to pivot said engagement means outwardly from said first position to at least one intermediate position, said control means being further operable to pivot said engagement means outwardly from said at least one intermediate position to said second position.

* * * * *